US00PP24250P2

(12) United States Plant Patent
Striem et al.

(10) Patent No.: US PP24,250 P2
(45) Date of Patent: Feb. 18, 2014

(54) GRAPEVINE PLANT NAMED 'SUGRAFORTYTWO'

(50) Latin Name: *Vitis vinifera*
Varietal Denomination: Sugrafortytwo

(75) Inventors: Michael J. Striem, Rehovot (IL); Terry A. Bacon, Bakersfield, CA (US)

(73) Assignee: Sun World International, LLC, Bakersfield, CA (US)

( * ) Notice: Subject to any disclaimer, the term of this patent is extended or adjusted under 35 U.S.C. 154(b) by 48 days.

(21) Appl. No.: 13/507,751

(22) Filed: Jul. 25, 2012

(51) Int. Cl.
*A01H 5/00* (2006.01)

(52) U.S. Cl.
USPC ..... Plt./205

(58) Field of Classification Search
USPC ..... Plt./205
See application file for complete search history.

*Primary Examiner* — Annette Para
(74) *Attorney, Agent, or Firm* — Knobbe, Martens, Olson & Bear, LLP

(57) ABSTRACT

A new and distinct grapevine variety is characterized in that it produces a large sized, green, oval berry with a large bunch size. The berries of 'Sugrafortytwo' are firm, very juicy, have high sugar content and a fruity flavor. Ripening of the new variety takes place about 1 month earlier than the comparable variety 'Sugrathirtyfive' (U.S. Plant Pat. No. 20,491) but the berry has similar shape and appearance. The new variety has an oval berry shape compared to the elongated shape for the comparable variety Thompson (unpatented), with similar ripening.

1 Drawing Sheet

Latin name of the genus and species claimed: *Vitis vinifera*. Variety denomination: 'SUGRAFORTYTWO'.

BACKGROUND AND SUMMARY OF THE INVENTION

This invention relates to the discovery and asexual propagation of a new and distinct variety of grapevine, 'Sugrafortytwo', as herein described and illustrated. The new variety was first hybridized in May 2004 by Michael J. Striem and evaluated in September 2008 by Michael J. Striem and from September 2009 through 2011 by Terry A. Bacon in Wasco, Kern County, Calif. The variety was originated by controlled hybridization.

The new variety 'Sugrafortytwo' is characterized by the production of a large sized, green, oval berry with a large bunch size. The berries of 'Sugrafortytwo' are firm, very juicy, have high sugar content and a fruity flavor.

The seed parent is the varietal selection '97148-027-365' (unpatented) and the pollen parent is the varietal selection 'Sugrathirtyone' (U.S. Plant Pat. No. 19,065). The parent varieties were first crossed in May 2004 by Michael J. Striem. The date of first sowing was March 2005, and the date of first flowering was May 2006.

The new variety 'Sugrafortytwo' was first asexually propagated in December 2008 in Wasco, Kern County, Calif., by Michael J. Striem using hardwood cuttings.

The new variety 'Sugrafortytwo' differs its seed parent '97148-027-365' (unpatented) in that the new variety ripens about 1 month earlier in the season, and the berry is oval compared to the elongated berry shape of the parent '97148-027-365' (unpatented).

The new variety 'Sugrafortytwo' differs from its pollen parent 'Sugrathirtyone' (U.S. Plant Pat. No. 19,065) in that the new variety ripens about 1 month earlier in the season.

The new variety 'Sugrafortytwo' resembles 'Thompson' (unpatented) in that it ripens about the same time. The new variety 'Sugrafortytwo' differs from 'Thompson' in that the new variety has an oval berry shape compared to an elongated berry shape for 'Thompson'. The new variety 'Sugrafortytwo' resembles 'Sugrathirtyfive' (U.S. Plant Pat. No. 20,491) in having the same berry shape and appearance. The new variety 'Sugrafortytwo' differs from 'Sugrathirtyfive' (U.S. Plant Pat. No. 20,491) in that it ripens about 1 month earlier in the season.

The new 'Sugrafortytwo' variety has been shown to maintain its distinguishing characteristics through successive asexual propagations by, for example, cuttings.

Variations of the usual magnitude from the characteristics described herein may occur with changes in any of a variety of factors such as growing conditions, irrigation, fertilization, pruning, management and with climatic variation.

BRIEF DESCRIPTION OF THE DRAWING

The accompanying color photographic illustration shows typical specimens of the foliage and fruit of the present new grape variety 'Sugrafortytwo'.

The illustration shows the upper and lower surface of the leaves and exterior and sectional view of the fruit.

The photographic illustration was taken shortly after the fruit was picked and the colors are as nearly true as is reasonably possible in a color representation of this type.

DETAILED DESCRIPTION OF THE PREFERRED EMBODIMENT

Throughout this specification, color names beginning with a small letter signify that the name of that color, as used in common speech, is aptly descriptive. Color names beginning with a capital letter designate values based upon The R.H.S. Colour Chart, published by The Royal Horticultural Society, London, England, 1986.

Many of the description values in this specification are based on and conform to those set forth by the International Board for Plant Genetic Resources Institute Grape Descriptors (*Vitis* spp.) of 1983 and/or 1997, which was developed in collaboration with the Office International de la Vigne et du Vin (OIV) and the International Union for the Protection of New Varieties of Plants (UPOV).

The descriptive matter which follows pertains to 'Sugrafortytwo' plants grown in the vicinity of Wasco, Kern County, Calif. during 2011, and is believed to apply to plants of the variety grown under similar conditions of soil and climate elsewhere.

VINE

General:

*Planting.*—Trained to a modified gable trellis, planted in about 7 ft.×12 ft. spacing.

*Practices.*—Gene-pool-vine: Cane pruned to approximately 36 spurs per vine. Test-vines: Cane pruned to approximately 36 spurs per vine.

*Size.*—Medium. Height: Medium, Approximately 2.0 m. Width: Approximately 2.2 m.

*Vigor.*—Medium.

*Fresh pruning weight.*—Approximately 7 kg per vine.

*Density of foliage.*—Medium.

*Productivity.*—Productive — approximately 36 clusters per vine after thinning.

*Yield.*—Approximately 34 kg per vine.

*Crop load.*—Approximately 4.9 kg per vine (kg fruit per kg fresh-pruning-weight).

*Own root.*—Yes.

*Resistance.*—Neither resistance nor susceptibility to diseases or pests has been observed in this variety.

Trunk:

*Shape.*—Circular.

*Diameter.*—Approximately 88 mm.

*Straps.*—Short.

*Surface texture.*—Shaggy.

*Inner bark color.*—Near Medium Greyed-Orange 165C.

*Outer bark color.*—Near Dark Greyed-green 197B.

SHOOTS

Young shoot:

*Form of tip.*—Half open.

*Distribution of anthocyanin coloration of tip.*—Striped.

*Intensity of anthocyanin coloration of tip.*—Weak.

*Density of prostrate hairs on tip.*—Medium.

*Density of erect hairs on tip.*—Absent.

Woody shoot (mature canes):

*Shape.*—Slender.

*Internode length.*—Approximately 50.6 mm.

*Width at node.*—Approximately 12.4 mm.

*Cross section.*—Circular.

*Surface.*—Smooth.

*Main color.*—Light brown, about Medium Greyed-Orange 164B.

*Lenticels.*—Absent.

*Density of erect hairs on nodes.*—Absent or Very Sparse.

*Density of erect hairs on internodes.*—Absent or Very Sparse.

*Growth of auxiliary shoots.*—Average 16.5 cm/shoot.

Flowering shoot:

*Vigor during flowering.*—Medium.

*Attitude during flowering on shoots which are not tied.*—Semi-erect.

*Color of dorsal side of internodes.*—Green with red highlights, about Medium Yellow-green 145A and Dark Greyed-purple 182A.

*Color of ventral side of internodes.*—Green with red highlights, about Medium Yellow-green 145A and Dark Greyed-purple 182A.

*Color of dorsal side of nodes.*—Green with red highlights, about Medium Yellow-green 145A and Dark Greyed-purple 182A.

*Color of ventral side of nodes.*—Green with red highlights, about Medium Yellow-green 145A and Dark Greyed-purple 182A.

*Density of erect hairs on nodes.*—Absent.

*Erect hairs on internode.*—Absent.

*Density of prostrate hairs on nodes.*—Absent.

*Density of prostrate hairs on internodes.*—Absent.

*Anthocyanin coloration of buds.*—Absent.

Tendrils:

*Distribution on the shoot at full flowering.*—Discontinuous.

*Thickness.*—Medium.

*Color.*—Near Medium Yellow-Green 144C.

*Form.*—Bifurcated.

*Number of consecutive tendrils.*—Up to 2.

*Length of tendril.*—Long, approximately 15 cm.

LEAVES

Young leaves:

*Color of upper surface of first* 4 *distal unfolded leaves.*—Near Medium Green 138A.

*Average intensity of anthocyanin coloration of six distal leaves prior to flowering.*—Absent.

*Density of prostrate hairs between veins at lower surface of* 4*th distal unfolded leaf.*—Absent.

*Density of erect hairs between veins at lower surface of* 4*th distal unfolded leaf.*—Absent.

*Density of prostrate hairs on veins at lower surface of* 4*th distal unfolded leaf.*—Absent.

*Density of erect hairs on veins at lower surface of* 4*th distal unfolded leaf.*—Absent.

Mature leaves:

*Average length.*—Approximately 135 mm from ending of petiole to tip of leaf.

*Average width.*—Approximately 175 mm.

*Size of blade.*—Medium.

*Shape of blade.*—Pentagonal.

*Number of lobes.*—Approximately 5.

*Anthocyanin coloration of main veins on the upper side of the blade.*—Absent or very faint.

*Mature leaf profile.*—Flat.

*Blistering surface of blade upper surface.*—Absent.

*Leaf blade tip.*—In the plane of the leaf.

*Undulation of margin.*—Slight.

*Thickness.*—Medium.

*Undulation of blade between main and lateral veins.*—Absent.

*Shape of teeth.*—Both sides concave.

*Length of teeth.*—Medium, usually 3 mm to 10 mm, average about 7.5 mm.

*Ratio length/width of teeth.*—Small.

*General shape of petiole sinus.*—Slightly open.

*Tooth at petiole sinus.*—Absent.

*Petiole sinus limited by veins.*—Absent.
*Shape of upper lateral sinus.*—Open.
*Depth of upper lateral sinus.*—Very Shallow.
*Density of prostrate hairs between veins on lower surface of blade.*—Absent.
*Density of erect hairs between veins on lower surface of blade.*—Absent.
*Density of prostrate hairs on main veins on lower surface of blade.*—Absent.
*Density of erect hairs on main veins on lower surface of blade.*—Absent.
*Density of prostrate hairs on main veins on upper surface of blade.*—Absent.
*Autumn coloration of leaves.*—Medium Yellow-green, about 153D, to Medium Greyed-yellow, about 162A.

Upper surface:
*Color.*—Near Medium Green 138A.
*Surface texture.*—Smooth.
*Surface appearance.*—Dull.
*Glossiness.*—Weak.
*Pubescence.*—Absent.

Lower surface:
*Color.*—Near Medium Green 135C.
*Anthocyanin coloration of main veins on lower leaf surface.*—Absent.
*Glossiness.*—Weak.
*Pubescence.*—Absent.
*Surface texture.*—Smooth.
*Surface appearance.*—Dull.

Petiole:
*Length of petiole.*—Medium, Approximately 7 cm.
*Length of petiole compared to middle vein.*—Shorter.
*Diameter.*—Approximately 3 mm.
*Density of prostrate hairs on petiole.*—Absent.
*Density of erect hairs on petiole.*—Absent.
*Shape of base of petiole sinus.*—U-shaped.
*Color.*—Medium Yellow-orange 20A to Medium Red 42C when exposed to sunlight.

Buds:
*Shape.*—Conical.
*Size.*—Medium, approximately 3 mm×4 mm.
*Position.*—Slightly held out.
*Cane bud fruitfulness.*—Basal most fruitful, $4^{th}$ to $5^{th}$ bud position.
*Time of bud burst.*—Medium, about Mar. 25, 2012.

FLOWERS

General:
*Flower sex.*—Hermaphrodite.
*Length of first inflorescence.*—Medium, about 18 cm.
*Position of first flowering node.*—Fourth node.
*Number of inflorescences per shoot.*—Approximately 1 to 2.
*Date of full bloom.*—Approximately May 10th.
*Size (diameter of fully open flower).*—Medium, approximately 6 mm.

FRUIT

General:
*Ripening period.*—Medium, starting about Jul. 24, 2012 with mid-ripe July 28.
*Use.*—Table grape fresh consumption.
*Keeping quality.*—Good.
*Shipping quality.*—Good.
*Date of first harvest.*—Approximately July $26^{th}$.
*Solids-sugar.*—High, about 20%.
*Refractometer test.*—Approximately 20%.
*Acid.*—Medium, approximately 0.60 gr./L tartaric acid.
*Juice pH.*—Approximately 3.5.
*Tendency to crack.*—Low.
*Sensitivity to sunburn.*—Medium.
*Fruit shrivel after ripe.*—Absent.
*Secondary cluster.*—Occasional.
*Resistance.*—Absent.

Cluster:
*Bunch size (peduncle excluded).*—Large.
*Bunch length (peduncle excluded).*—Medium, approximately 30 cm.
*Bunch width.*—Approximately 22 cm.
*Bunch weight.*—High, approximately 1000 g.
*Bunch density.*—High.
*Number of berries.*—Approximately 129.
*Form.*—Africa-shaped.

Peduncle:
*Length of peduncle.*—Medium, approximately 40 mm.
*Lignification of peduncle.*—Absent.
*Color.*—Near Medium Yellow-green 144B to Medium Red 42C.

Berry:
*Size.*—Large.
*Uniformity of size.*—Uniform.
*Berry weight.*—Heavy, approximately 6.7 gr. treated.
*Gibberellic acid treated.*—Medium, 10 ppm to 20 ppm.
*Shape.*—Oval.
*Presence of seeds.*—Rudimentary.
*Cross section.*—Round.
*Dimensions.*—Longitudinal axis: Approximately 24 mm treated. Horizontal axis: Approximately 20 mm treated.
*Skin color (without bloom).*—Near Medium Yellow-green 144D.
*Flesh color.*—Near Light Yellow-green 145D.
*Juiciness of flesh.*—Very juicy.
*Berry firmness.*—Firm.
*Particular flavor.*—Fruity.
*Bloom (cuticular wax).*—Medium.
*Pedicel length.*—Medium approximately 8 mm.
*Berry separation from pedicel.*—Medium.
*Visibility of hilum.*—Slightly.

Skin:
*Thickness.*—Medium.
*Texture.*—Smooth.
*Reticulation.*—Absent.
*Roughness.*—Absent.
*Tenacity.*—Tenacious to flesh.

Seed:
*Number of seeds per berry.*—Usually 1, sometimes 2.
*Size.*—Small.
*Color.*—Near Light Green 145A.
*Texture.*—Soft.
*Endosperm.*—Slight.
*Fresh weight of seed-traces/berry.*—Approximately 16.5 mg.
*Room-dry weight of seed-traces/berry.*—Approximately 4.1 mg.

What is claimed is:

1. A new and distinct variety of grapevine as herein illustrated and described.

* * * * *

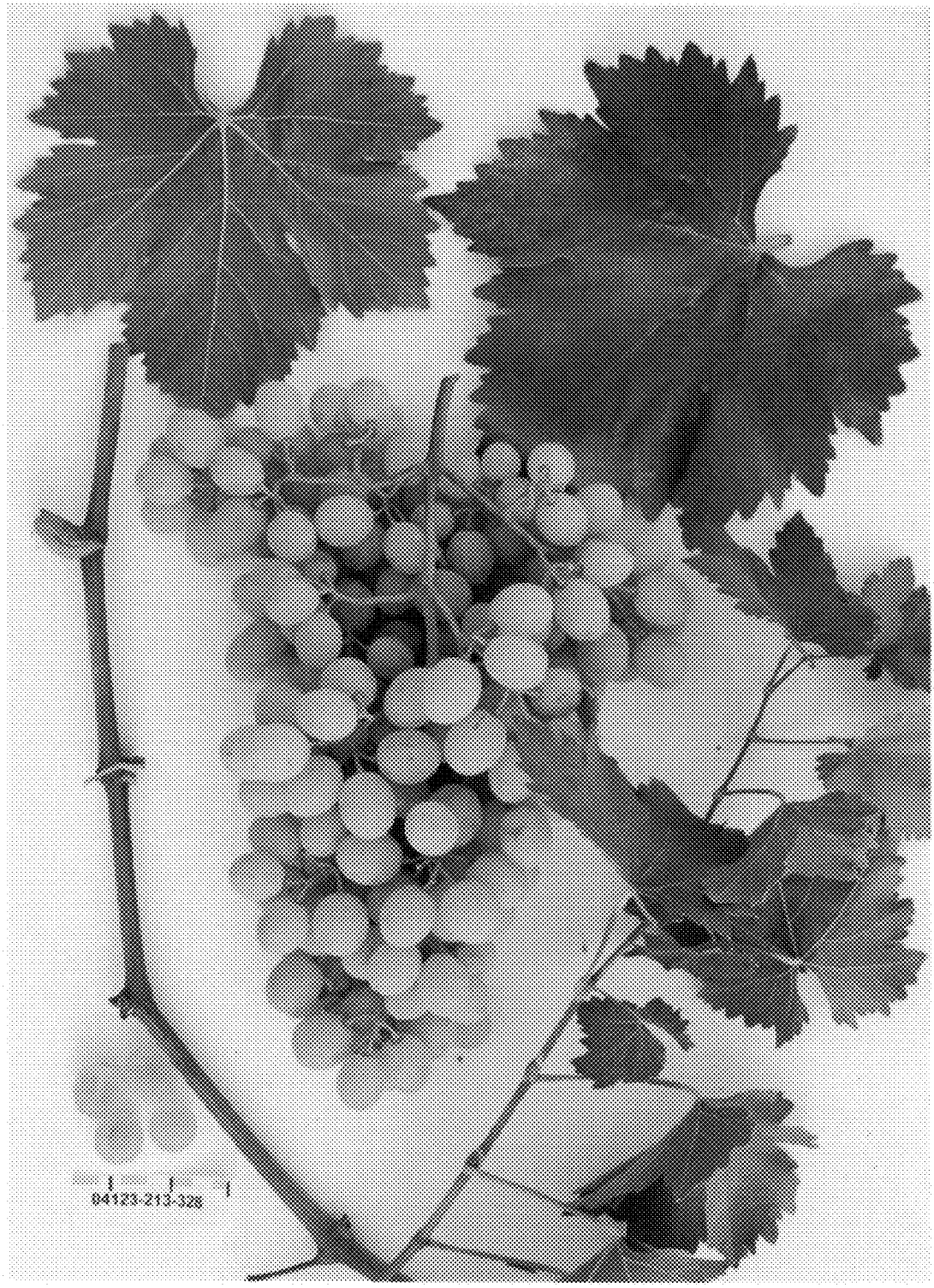
04123-213-328